United States Patent
Singh

(10) Patent No.: US 12,412,212 B2
(45) Date of Patent: Sep. 9, 2025

(54) DATA SECURITY IN ENROLLMENT MANAGEMENT SYSTEMS

(71) Applicant: Optum Technology, Inc., Eden Prairie, MN (US)

(72) Inventor: Priyanka Singh, Rudraprayag (IN)

(73) Assignee: Optum Technology, Inc., Eden Prairie, MN (US)

( * ) Notice: Subject to any disclaimer, the term of this patent is extended or adjusted under 35 U.S.C. 154(b) by 398 days.

(21) Appl. No.: 17/454,650

(22) Filed: Nov. 12, 2021

(65) Prior Publication Data

US 2022/0067832 A1 Mar. 3, 2022

Related U.S. Application Data

(63) Continuation of application No. 16/669,634, filed on Oct. 31, 2019, now Pat. No. 11,210,737.

(51) Int. Cl.
*G06Q 40/04* (2012.01)
*G16H 10/60* (2018.01)

(52) U.S. Cl.
CPC .............. *G06Q 40/04* (2013.01); *G16H 10/60* (2018.01)

(58) Field of Classification Search
CPC ............................... G06Q 40/04; G16H 10/60
See application file for complete search history.

(56) References Cited

U.S. PATENT DOCUMENTS

| 6,154,732 | A | 11/2000 | Tarbox |
| 7,912,734 | B2 | 3/2011 | Kil |
| 9,064,284 | B1 | 6/2015 | Janiszeski et al. |

(Continued)

FOREIGN PATENT DOCUMENTS

| WO | WO-2004017169 A2 | * 2/2004 | ............. G06Q 40/00 |
| WO | WO-2008143374 A1 | * 11/2008 | ............. G06Q 40/04 |
| WO | 2013/052733 A1 | 4/2013 | |

OTHER PUBLICATIONS

"Save Time and Money On Health Insurance." pp. 1-3, [online], [retrieved from the Internet Jan. 17, 2020] <URL: https://www.stridehealth.com/coverage>.
"See If You Can Still Get Or Change 2020 Health Coverage." HealthCare.gov, pp. 1-2, [online], [retrieved from the Internet Jan. 17, 2020] <URL: https://www.healthcare.gov/screener/>.

(Continued)

*Primary Examiner* — Daniel S Felten
(74) *Attorney, Agent, or Firm* — Alston & Bird LLP

(57) ABSTRACT

There is a need for improving data security in enrollment management systems. This need can be addressed by, for example, solutions for determining an enrollment recommendation for a primary member profile based on preconfigured enrollment modeling data. In one example, a method includes retrieving enrollment modeling data for a group of member profiles, determining a plurality of related member profiles for the primary member profile from the group of member profiles, determining a cross-member enrollment prediction for the primary member profile by comparing enrollment modeling data of the primary member profile and enrollment modeling data of each related member profile, determining a member-specific enrollment recommendation by comparing enrollment modeling data of the primary member profile and enrollment coverage criteria for each enrollment plan, and determining the enrollment recommendation based on the cross-member enrollment prediction and the member-specific enrollment prediction.

20 Claims, 9 Drawing Sheets

(56) References Cited

U.S. PATENT DOCUMENTS

| | | | |
|---|---|---|---|
| 9,330,183 B2* | 5/2016 | Woss | G06F 16/9535 |
| 9,342,798 B2* | 5/2016 | Breckenridge | H04L 67/02 |
| 9,715,596 B2* | 7/2017 | Woss | H04L 67/02 |
| 9,946,772 B2* | 4/2018 | Rubinstein | G06F 16/9024 |
| 9,984,073 B2* | 5/2018 | Auger | G09B 5/00 |
| 10,049,099 B2* | 8/2018 | Zhu | G06F 16/3322 |
| 10,423,240 B2* | 9/2019 | Ryu | G06F 3/0237 |
| 10,467,282 B2* | 11/2019 | Shorman | G06Q 50/01 |
| 10,592,837 B2* | 3/2020 | Sinha | G06F 21/55 |
| 10,671,661 B2* | 6/2020 | Schrock | G06F 16/951 |
| 10,877,633 B2* | 12/2020 | Boucher | G06F 16/2228 |
| 2001/0032156 A1 | 10/2001 | Candura et al. | |
| 2002/0073005 A1 | 6/2002 | Welnicki et al. | |
| 2004/0111349 A1 | 6/2004 | Charnley | |
| 2004/0138989 A1* | 7/2004 | O'Malley | G07C 9/29 705/37 |
| 2005/0192895 A1* | 9/2005 | Rogers | G07F 7/08 705/16 |
| 2006/0178915 A1 | 8/2006 | Chao | |
| 2007/0130043 A1 | 6/2007 | O'Shaughnessy et al. | |
| 2010/0005035 A1 | 1/2010 | Carpenter et al. | |
| 2012/0173265 A1 | 7/2012 | Brush et al. | |
| 2016/0034970 A1 | 2/2016 | Musil et al. | |
| 2016/0247072 A1* | 8/2016 | Auger | G06F 16/00 |
| 2016/0299883 A1* | 10/2016 | Zhu | G06F 40/232 |
| 2017/0243278 A1* | 8/2017 | Hyde | G06Q 40/06 |
| 2018/0040086 A1 | 2/2018 | Desai et al. | |
| 2018/0350016 A1 | 12/2018 | Ward | |
| 2019/0080416 A1 | 3/2019 | Smith et al. | |
| 2019/0102722 A1 | 4/2019 | Chetlur et al. | |
| 2019/0385199 A1 | 12/2019 | Bender et al. | |
| 2020/0185101 A1 | 6/2020 | Selker et al. | |
| 2020/0372561 A1 | 11/2020 | Sanghavi et al. | |

OTHER PUBLICATIONS

"We Took Health Insurance Apart. Now It Works." Bind, pp. 1-5, [online], [retrieved from the Internet Jan. 17, 2020] <https://www.yourbind.com/>.

Dietsche, Erin, "This Startup Is Daring To Bring On-Demand Services To Health Insurance." MedCity News, pp. 1-11, [online], [retrieved from the Internet Jan. 17, 2019] <URL: https://medcitynews.com/2018/08/on-demand-health-insurance/?rf=1>.

\* cited by examiner

Prepare output:
Total member in low usage: X
Total member in medium usage: Y — 901
Total member in high usage: Z

| Usage group | Location | Plan | Most used Drugs covered? | Most used Providers covered? |
|---|---|---|---|---|
| Low<br><br>902 | XYZ<br><br>903 | PLANA1<br><br>904 | Drug1: Yes<br>Drug2: No<br>Drug3: Yes   905<br>Drug4: Yes<br>Drug5: Yes<br>Drug6: Yes | Provider1: Yes<br>Provider2: Yes<br>Provider3: Yes   906<br>Provider4: Yes<br>Provider5: Yes<br>Provider6: Yes |

FIG. 9

DATA SECURITY IN ENROLLMENT MANAGEMENT SYSTEMS

CROSS-REFERENCE TO RELATED APPLICATIONS

This application is a continuation of U.S. application Ser. No. 16/669,634, filed Oct. 31, 2019, which is hereby incorporated herein in its entirety by reference.

BACKGROUND

Various embodiments of the present invention address technical challenges related to improving data security in enrollment management systems. Existing enrollment management systems suffer from major data security shortcomings. Various embodiments of the present address the data security shortcomings of the noted enrollment management systems and disclose various techniques for improving data security in various kinds of enrollment management systems.

BRIEF SUMMARY

In general, embodiments of the present invention provide methods, apparatus, systems, computing devices, computing entities, and/or the like for improving data security in enrollment management systems by enabling techniques that utilize preconfigured data (e.g., preconfigured enrollment modeling data and preconfigured plan definition data) to determine enrollment recommendations for various member profiles by a remote enrollment management system that communicates with client computing entities of the various member profiles remotely and over a communication network.

In accordance with one aspect, a method is provided. In one embodiment, the method comprises: accessing, in response to receiving an enrollment recommendation request for an enrollment recommendation and from a preconfigured enrollment modeling database, enrollment modeling data for each member profile of a plurality of member profiles, wherein: (i) the enrollment modeling data for each member profile of the plurality of member profiles comprises one or more transactional records for the corresponding member profile and one or more demographic features for the corresponding member profile, (ii) receiving the enrollment recommendation request initiates a remote enrollment recommendation session, and (iii) none of the enrollment modeling data are obtained from the remote end-user during the remote enrollment recommendation session; identifying one or more related member profiles of the plurality member profiles based at least in part on comparing the enrollment modeling data for a primary member profile of the plurality of member profiles and the enrollment modeling data for each secondary member profile of the plurality of member profiles other than the primary member profile; generating, during the remote enrollment recommendation session, a trained cross-member enrollment prediction model based at least in part on one or more training features for each related member profile of the plurality of related member profiles, wherein: (i) the one or more training features for a particular related member profile of the one or more related member profile are determined based at least in part on the enrollment modeling data for the particular related member profile, and (ii) generating the trained cross-member enrollment prediction model is performed without requiring any user input from the remote end-user; determining a cross-member enrollment recommendation for the primary member profile based at least in part on processing one or more cross-member predictive features of the primary member profile using the trained cross-member enrollment model, wherein the one or more cross-member predictive features are determined based at least in part on the enrollment modeling data for the primary member profile; determining a member-specific enrollment recommendation for the primary member profile based at least in part on one or more member-specific features of the primary member profile and one or more enrollment coverage criteria for each enrollment plan of the plurality of enrollment plans, wherein the one or more member-specific features are determined based at least in part on the enrollment modeling data for the primary member profile; determining the enrollment recommendation for the primary member profile based at least in part on the cross-member enrollment recommendation for the primary member profile and the member-specific enrollment recommendation for the primary member profile; and displaying, during the during the remote enrollment recommendation session and to a remote client device of the remote end-user, an enrollment recommendation user interface associated with the enrollment recommendation.

In accordance with another aspect, a computer program product is provided. The computer program product may comprise at least one computer-readable storage medium having computer-readable program code portions stored therein, the computer-readable program code portions comprising executable portions configured to: access, in response to receiving an enrollment recommendation request for an enrollment recommendation and from a preconfigured enrollment modeling database, enrollment modeling data for each member profile of a plurality of member profiles, wherein: (i) the enrollment modeling data for each member profile of the plurality of member profiles comprises one or more transactional records for the corresponding member profile and one or more demographic features for the corresponding member profile, (ii) receiving the enrollment recommendation request initiates a remote enrollment recommendation session, and (iii) none of the enrollment modeling data are obtained from the remote end-user during the remote enrollment recommendation session; identify one or more related member profiles of the plurality member profiles based at least in part on comparing the enrollment modeling data for a primary member profile of the plurality of member profiles and the enrollment modeling data for each secondary member profile of the plurality of member profiles other than the primary member profile; generate, during the remote enrollment recommendation session, a trained cross-member enrollment prediction model based at least in part on one or more training features for each related member profile of the plurality of related member profiles, wherein: (i) the one or more training features for a particular related member profile of the one or more related member profile are determined based at least in part on the enrollment modeling data for the particular related member profile, and (ii) generating the trained cross-member enrollment prediction model is performed without requiring any user input from the remote end-user; determine a cross-member enrollment recommendation for the primary member profile based at least in part on processing one or more cross-member predictive features of the primary member profile using the trained cross-member enrollment model, wherein the one or more cross-member predictive features are determined based at least in part on the enrollment modeling data for the primary member profile; determining a member-specific enrollment recommendation for the primary member profile based at least in part on one or more member-specific features of the primary member profile and one or more enrollment coverage criteria for each enrollment plan of the plurality of enrollment plans, wherein the one or more member-specific features are determined based at least in part on the enrollment modeling data for the primary member profile; determine the enrollment recommendation for the primary member profile based at least in part on the cross-member enrollment recommendation for the primary member profile and the member-specific enrollment recommendation for the primary member profile; and display, during the during the remote enrollment recommendation session and to a remote client device of the remote end-user, an enrollment recommendation user interface associated with the enrollment recommendation.

In accordance with yet another aspect, an apparatus comprising at least one processor and at least one memory including computer program code is provided. In one embodiment, the at least one memory and the computer program code may be configured to, with the processor, cause the apparatus to: access, in response to receiving an enrollment recommendation request for an enrollment recommendation and from a preconfigured enrollment modeling database, enrollment modeling data for each member profile of a plurality of member profiles, wherein: (i) the enrollment modeling data for each member profile of the plurality of member profiles comprises one or more transactional records for the corresponding member profile and one or more demographic features for the corresponding member profile, (ii) receiving the enrollment recommendation request initiates a remote enrollment recommendation session, and (iii) none of the enrollment modeling data are obtained from the remote end-user during the remote enrollment recommendation session; identify one or more related member profiles of the plurality member profiles based at least in part on comparing the enrollment modeling data for a primary member profile of the plurality of member profiles and the enrollment modeling data for each secondary member profile of the plurality of member profiles other than the primary member profile; generate, during the remote enrollment recommendation session, a trained cross-member enrollment prediction model based at least in part on one or more training features for each related member profile of the plurality of related member profiles, wherein: (i) the one or more training features for a particular related member profile of the one or more related member profile are determined based at least in part on the enrollment modeling data for the particular related member profile, and (ii) generating the trained cross-member enrollment prediction model is performed without requiring any user input from the remote end-user; determine a cross-member enrollment recommendation for the primary member profile based at least in part on processing one or more cross-member predictive features of the primary member profile using the trained cross-member enrollment model, wherein the one or more cross-member predictive features are determined based at least in part on the enrollment modeling data for the primary member profile; determining a member-specific enrollment recommendation for the primary member profile based at least in part on one or more member-specific features of the primary member profile and one or more enrollment coverage criteria for each enrollment plan of the plurality of enrollment plans, wherein the one or more member-specific features are determined based at least in part on the enrollment modeling data for the primary member profile; determine the enrollment recommendation for the primary member profile based at least in part on the cross-member enrollment recommendation for the primary member profile and the member-specific enrollment recommendation for the primary member profile; and display, during the during the remote enrollment recommendation session and to a remote client device of the remote end-user, an enrollment recommendation user interface associated with the enrollment recommendation.

BRIEF DESCRIPTION OF THE DRAWINGS

Figure 1:
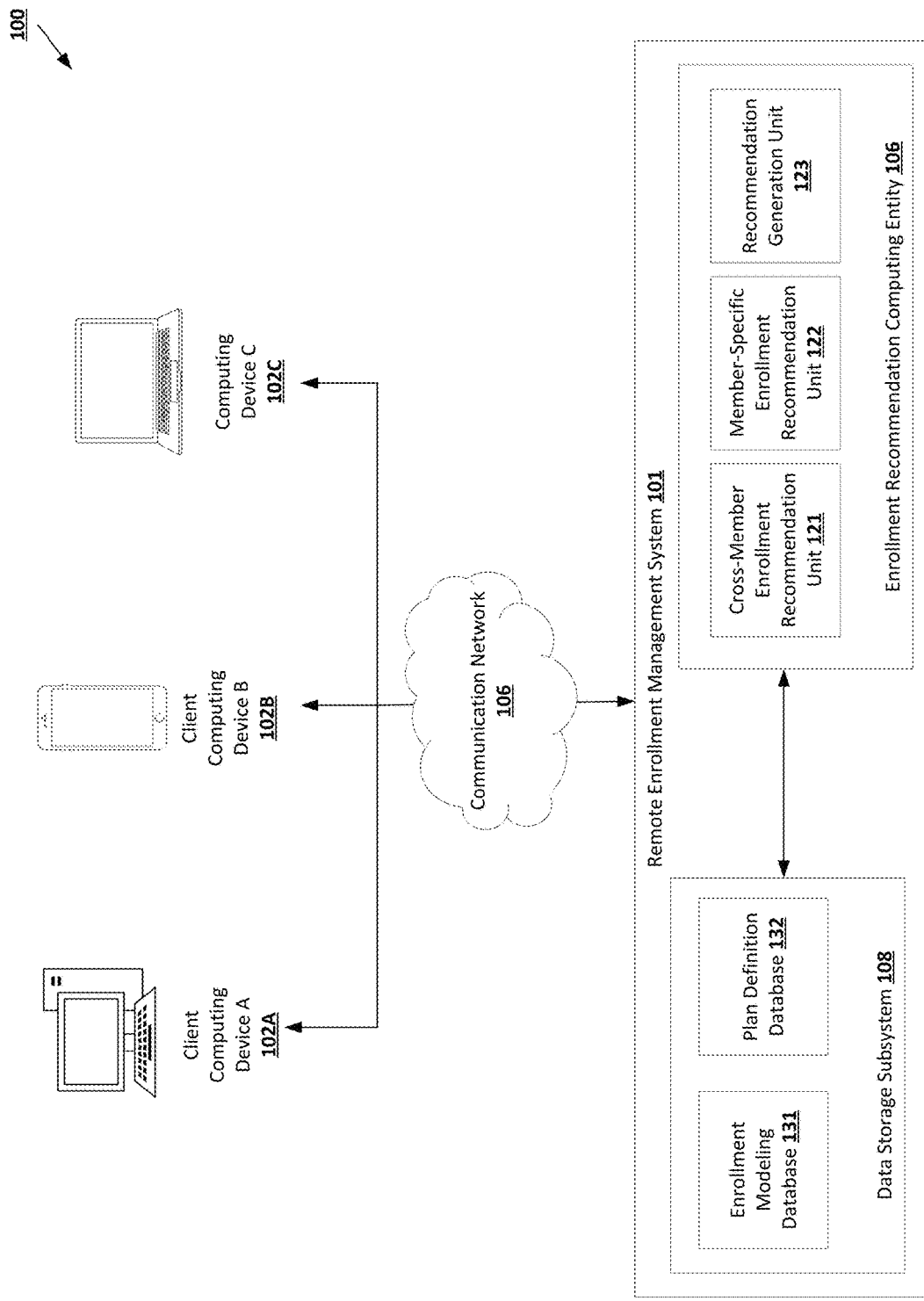

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
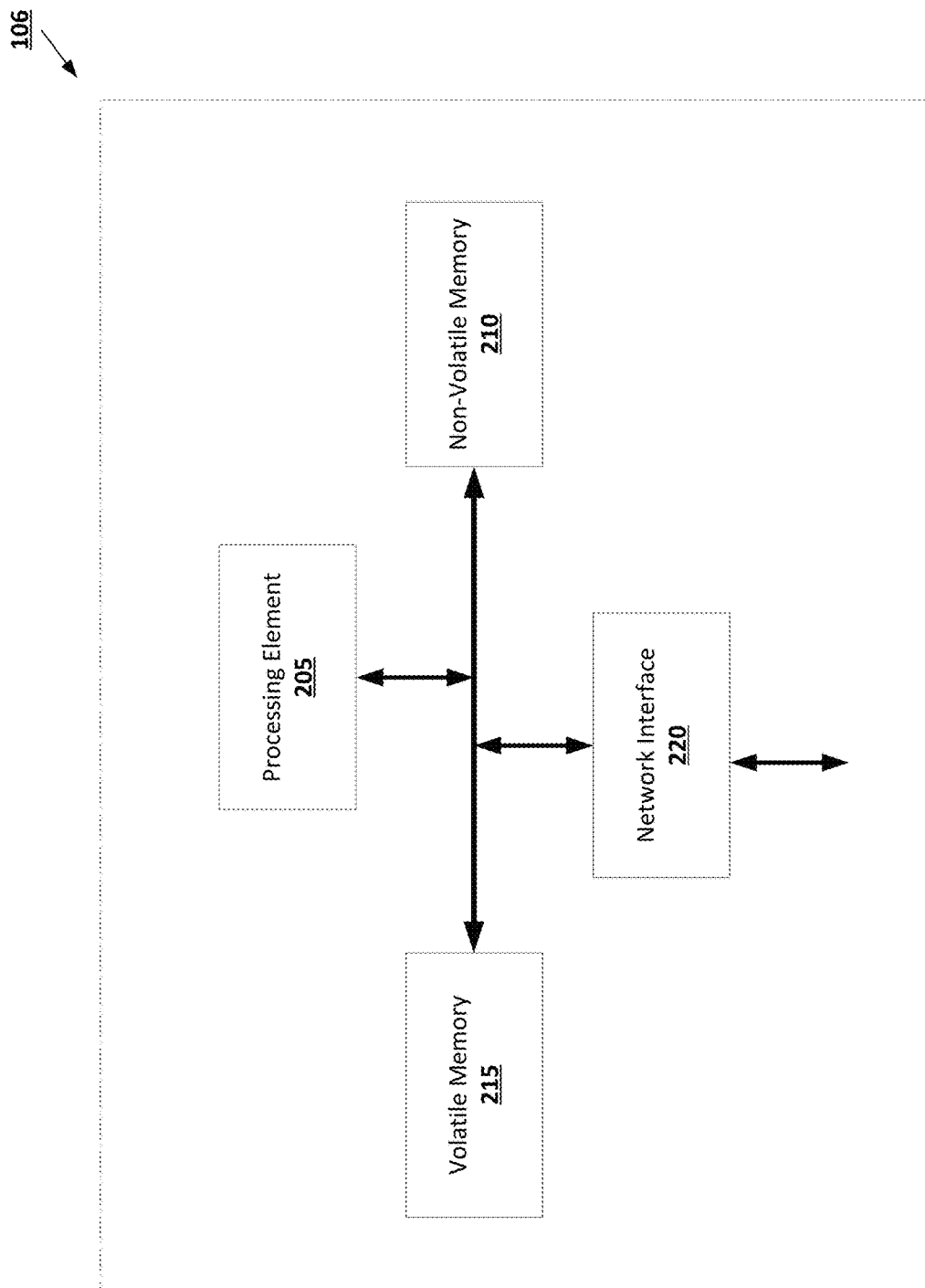

FIG. 2 provides an example enrollment recommendation computing entity in accordance with some embodiments discussed herein.

Figure 3:
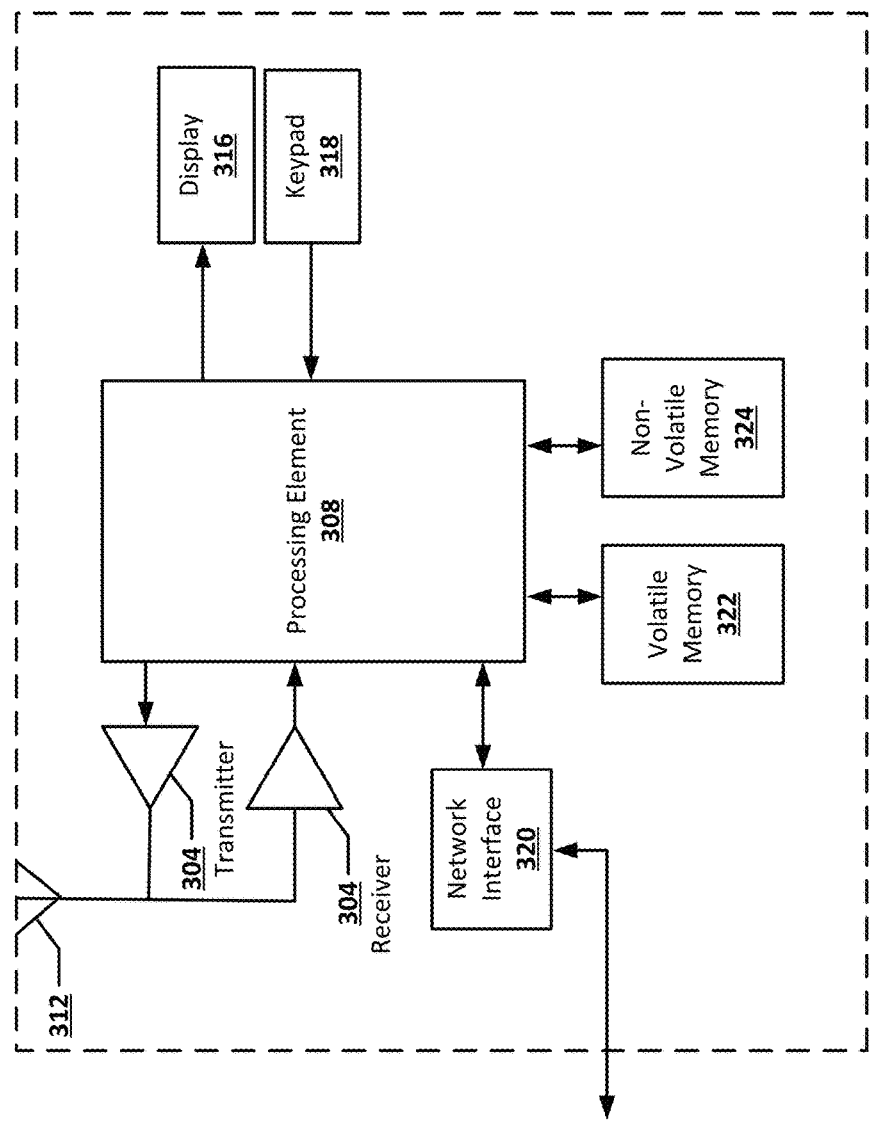

FIG. 3 provides an example client computing entity in accordance with some embodiments discussed herein.

Figure 4:
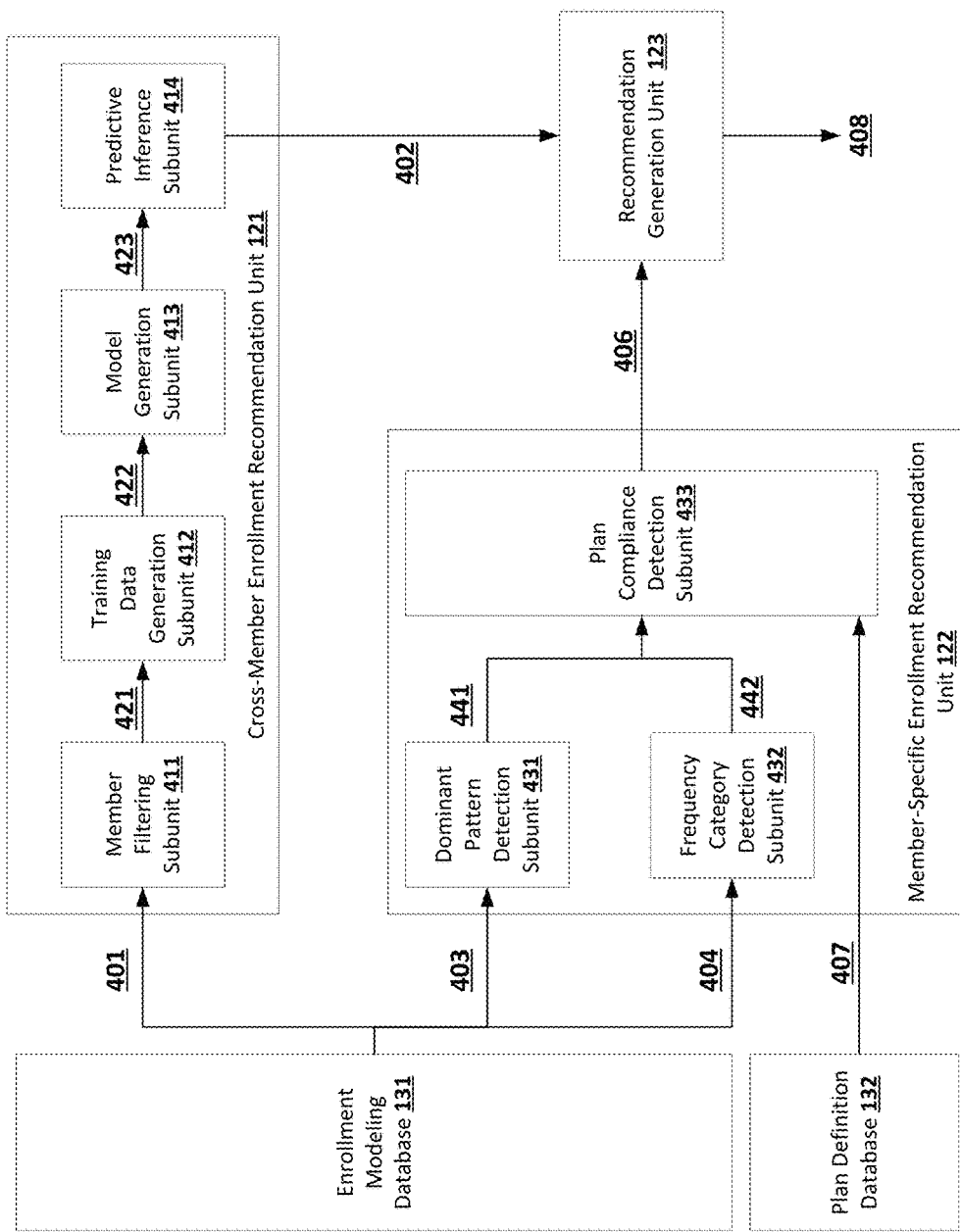

FIG. 4 is a data flow diagram of an example process for remotely determining an enrollment recommendation in accordance with some embodiments discussed herein.

Figure 5:
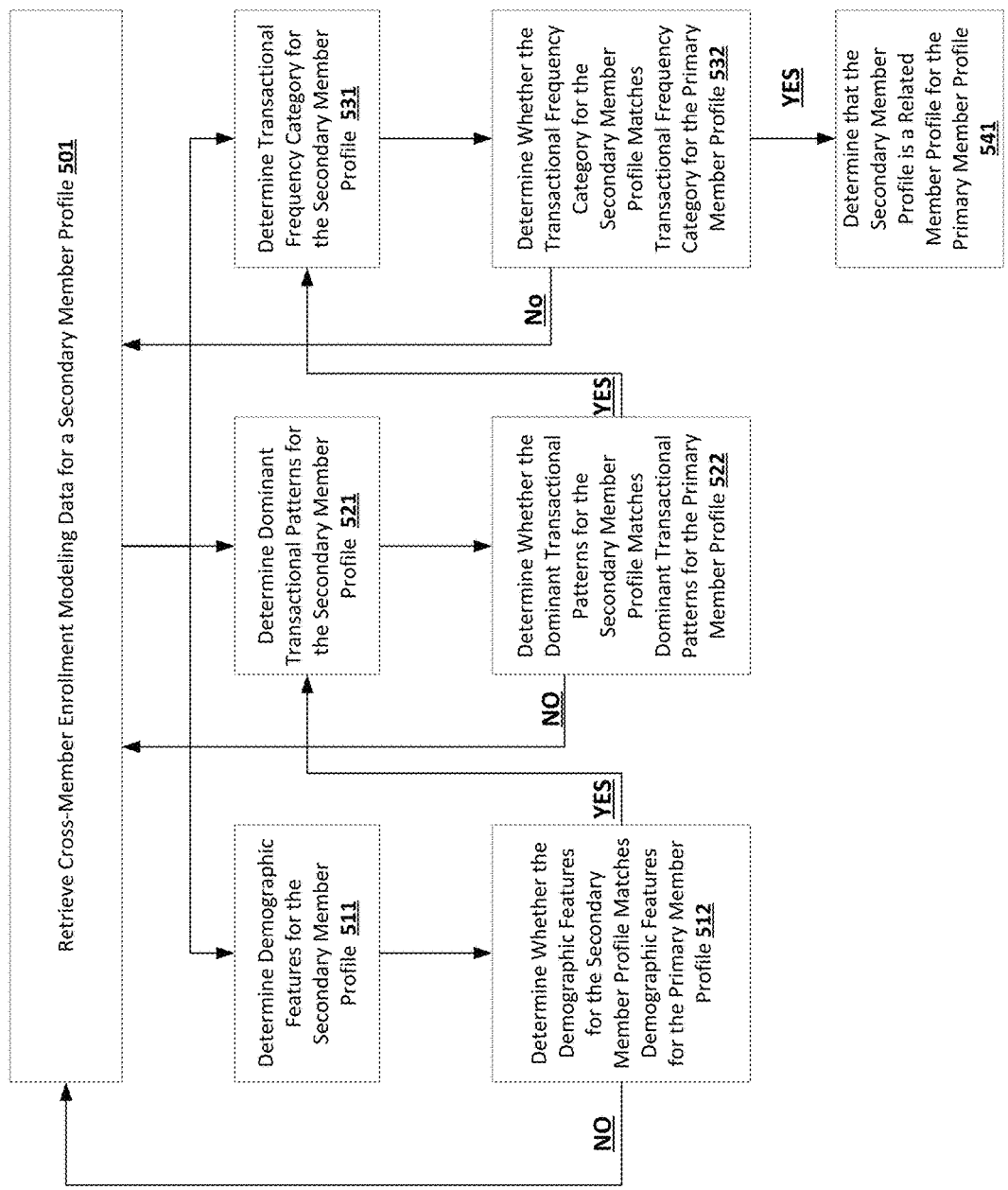

FIG. 5 is a flowchart diagram of an example process for determining related member profiles for a primary member profile in accordance with some embodiments discussed herein.

Figure 6:
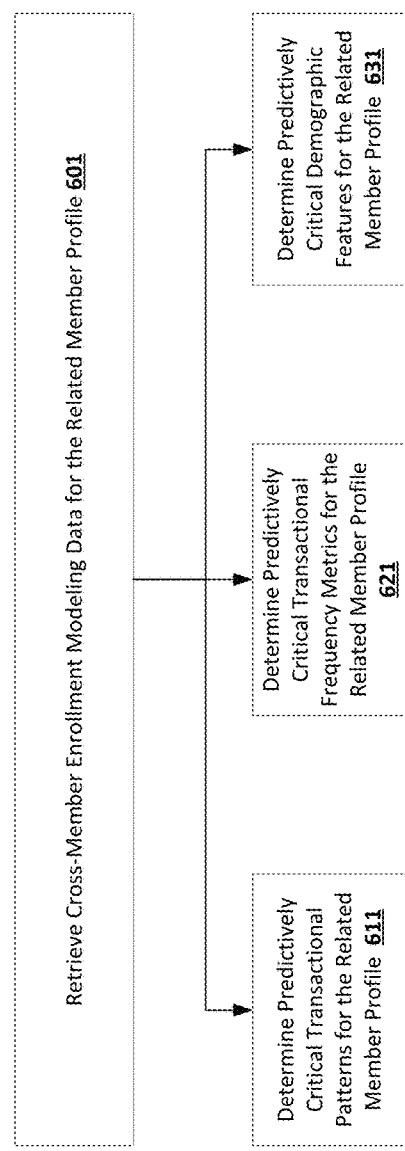

FIG. 6 is a flowchart diagram of an example process for generating training features for a related member profile in accordance with some embodiments discussed herein.

Figure 7:
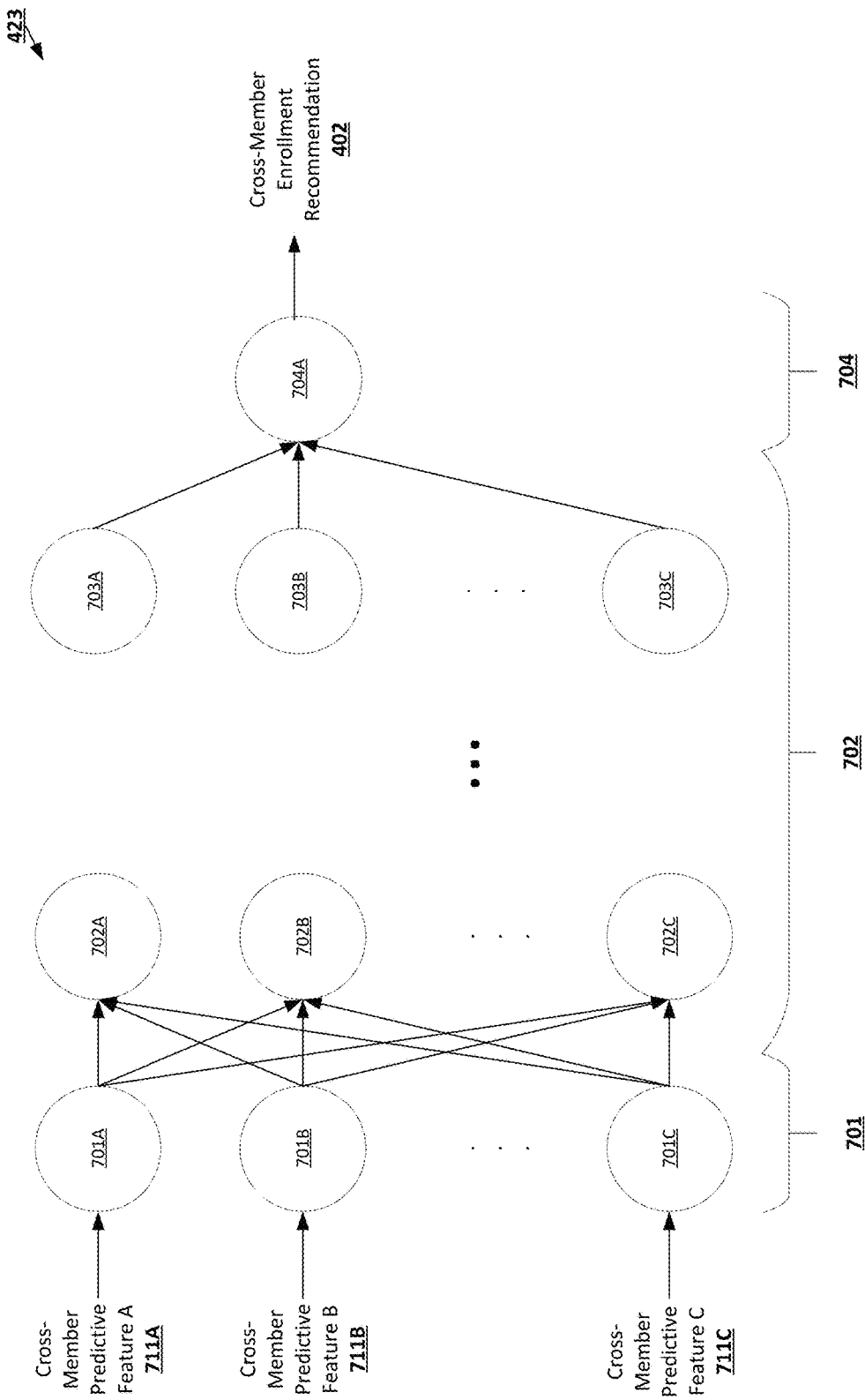

FIG. 7 is an operational example of a cross-member enrollment recommendation model in accordance with some embodiments discussed herein.

Figure 8:
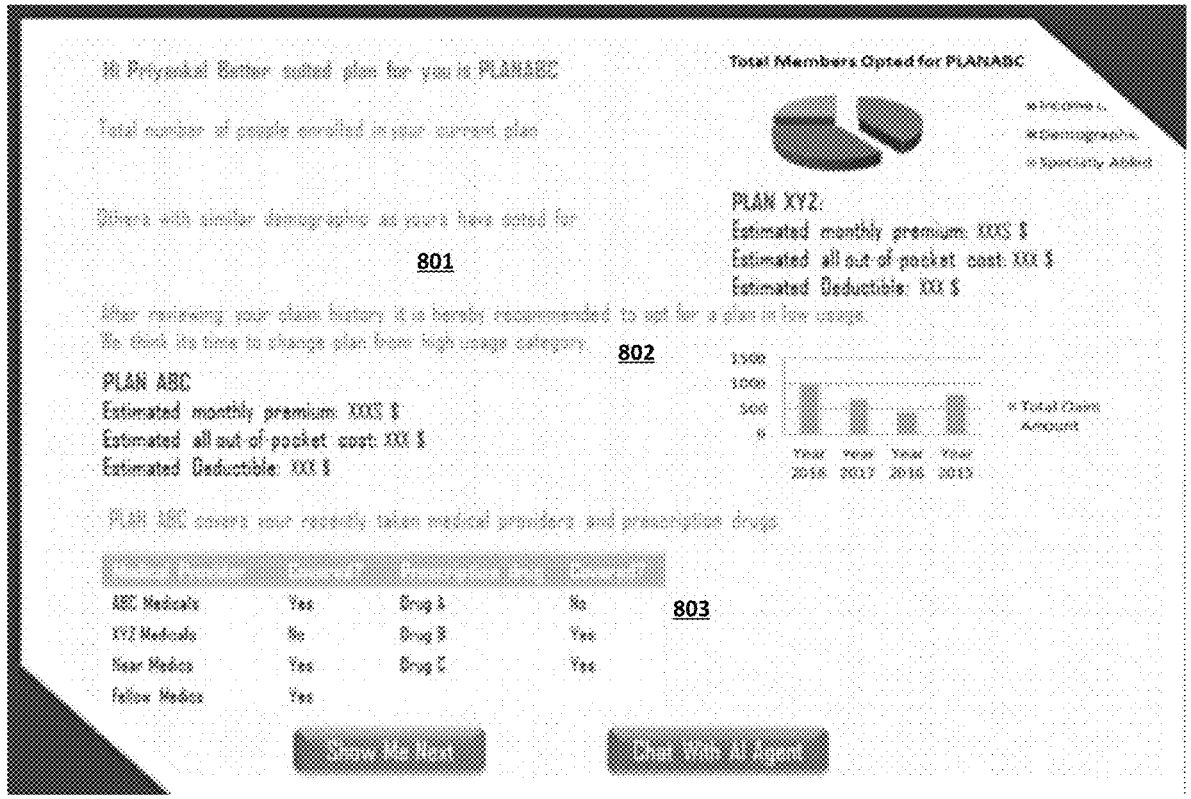

FIG. 8 is an operational example of an enrollment recommendation user interface in accordance with some embodiments discussed herein.

FIG. 9 is an operational example of a recommended plan information user interface in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. OVERVIEW

Operations of various existing remote enrollment management systems, such as various existing systems configured to generate health insurance recommendations for various member profiles, typically require transmission of vast amount of data, including vast amounts of patient health information and/or patient identifying information, over communication networks and during plan recommendation sessions. This need for transmission of vast amounts of sensitive data in real-time exposes existing enrollment management systems to various security challenges, as any penetration into the communication networks and/or into the computer devices in such systems can have substantial negative consequences for the security and integrity of user-supplied data as well as for reliability of the enrollment recommendations generated based on user-supplied data. Moreover, the need for user input and transmission of vast amounts of data may undermine user experience quality and create latency for the remote enrollment management systems, as such systems incur substantial wait times associated with periods of receiving user-supplied data after user input of particular relevant input data. Thus, various existing remote enrollment management systems suffer from substantial security, reliability, user experience quality, and efficiency challenges that result from the need of such systems to receive vast amounts of user-supplied data during plan recommendation sessions.

To address the above-noted challenges associated with the security, reliability, user experience quality, and efficiency of various existing remote enrollment management systems, various embodiments of the present invention disclose techniques for performing enrollment recommendation based on preconfigured data stored locally on the remote enrollment management systems. Examples of the preconfigured data include demographic data associated with various member profiles, claim history data associated with various member profile, and/or the like. The disclosed embodiments utilize the preconfigured data to generate at least one of two sets of enrollment recommendations: enrollment recommendations based on comparing demographic features and transactional patterns across various members and enrollment recommendations based on comparing demographic features and transactional patterns on a per-member basis and vis-à-vis enrollment criteria for various health insurance plans.

By utilizing the above-noted techniques, various embodiments of the present invention enable reducing the need for real-time transmission of user-supplied input data prior to performing enrollment recommendation. In doing so, various embodiments of the present invention reduce the chance for exposure of sensitive member data to network security challenges by increasing use of locally-stored enrollment modeling data and plan definition data to generate enrollment recommendations. Moreover, increasing use of locally-stored enrollment modeling data and plan definition data to generate enrollment recommendations further eliminates delays associated with user input and transmission of data, thus increasing efficiency of enrollment management systems as well as enhancing user experience quality in such enrollment management systems. Thus, by disclosing techniques for increasing use of locally-stored enrollment modeling data and plan definition data to generate enrollment recommendations and thus reducing the need for real-time transmission of user-supplied input data prior to performing enrollment recommendation, various embodiments of the present invention make important technical contributions to security, reliability, user experience quality, and efficiency of the enroll management systems.

II. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating-junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

FIG. 1 is a schematic diagram of an example architecture 100 for determining enrollment recommendations for various member profiles of a remote enrollment management system 101. The architecture 100 includes one or more client computing entities each configured to enable one or more member profiles to interact with the remote enrollment management system 101 over a communication network 106. For example, the architecture 100 may enable various member profiles to remotely utilize the remote enrollment management system 101 to obtain recommendations for suitable health insurance plans based on patient data (e.g., patient demographic data, patient health insurance claim history data, and/or the like) maintained by the remote enrollment management system 101. The communication network 106 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The remote enrollment management system 101 includes an enrollment recommendation computing entity 106 and a storage subsystem 108. The enrollment recommendation computing entity 106 is configured to generate enrollment recommendations based on data stored in the storage subsystem 108. The data stored in the storage subsystem 108 include enrollment modeling data in the enrollment modeling database 131 and plan definition data in the plan definition database 132. The enrollment modeling data include information about transactional behaviors and/or demographic features of the member profiles associated with the remote enrollment management system 101, while the plan definition data include information about enrollment criteria (e.g., enrollment conditions, payment conditions, coverage criteria, and/or the like) of various enrollment plans (e.g., health insurance plans) whose respective member enrollment is managed by the remote enrollment management system 101.

The enrollment recommendation computing entity 106 includes a cross-member enrollment recommendation unit 121, a member-specific enrollment recommendation unit 122, and a recommendation generation unit 123. The cross-member enrollment recommendation unit 121 may be configured to retrieve enrollment modeling data from the enrollment modeling database 131 and process the retrieved enrollment modeling data to generate cross-member enrollment recommendations for various member profiles, where the cross-member enrollment recommendation for a particular member profile may indicate one or more selected enrollment plans of a plurality of enrollment plans for the particular member profile based on similarities in the enrollment modeling data for a pool of various member profiles associated with the remote enrollment management system 101. The member-specific enrollment recommendation unit 122 may be configured to retrieve enrollment modeling data from the enrollment modeling database 131 and process the retrieved enrollment modeling data to generate member-specific enrollment recommendations, where the member-specific enrollment recommendation for a particular member profile one or more selected enrollment plans of a plurality of enrollment plans for the particular member profile determined based on transactional behaviors and/or demographic features of the particular member profile irrespective of the similarities among the pool of member profiles associated with the remote enrollment management system 101. The recommendation generation unit 123 is configured to generate the enrollment recommendations as well as one or more user interfaces configured to display information about the generated enrollment recommendations.

Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Enrollment Recommendation Computing Entity

FIG. 2 provides a schematic of an enrollment recommendation computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the enrollment recommendation computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the enrollment recommendation computing entity 106 may include or be in communication with one or more processing elements 205 (also referred to as processors, processing circuitry, and/or similar terms used herein interchangeably) that communicate with other elements within the enrollment recommendation computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the enrollment recommendation computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the enrollment recommendation computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the enrollment recommendation computing entity 106 with the assistance of the processing element 205 and operating system.

As indicated, in one embodiment, the enrollment recommendation computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOC SIS), or any other wired transmission protocol. Similarly, the enrollment recommendation computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the enrollment recommendation computing entity 106 may include or be in communication with one or more input elements, such as a keyboard input, a mouse input, a touch screen/display input, motion input, movement input, audio input, pointing device input, joystick input, keypad input, and/or the like. The enrollment recommendation computing entity 106 may also include or be in communication with one or more output elements (not shown), such as audio output, video output, screen/display output, motion output, movement output, and/or the like.

Exemplary Client Computing Entity

FIG. 3 provides an illustrative schematic representative of a client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the enrollment recommendation computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the enrollment recommendation computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the enrollment recommendation computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the enrollment recommendation computing entity 106 and/or various other computing entities.

In another embodiment, the client computing entity 102 may include one or more components or functionality that are the same or similar to those of the enrollment recommendation computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

IV. EXEMPLARY SYSTEM OPERATIONS

Operations of various existing remote enrollment management systems, such as various existing systems configured to generate health insurance recommendations for various member profiles, typically require transmission of vast amount of data, including vast amounts of patient health information and/or patient identifying information, over communication networks and during plan recommendation sessions. This need for transmission of vast amounts of sensitive data in real-time exposes existing enrollment management systems to various security challenges, as any penetration into the communication networks and/or into the computer devices in such systems can have substantial negative consequences for the security and integrity of user-supplied data as well as for reliability of the enrollment recommendations generated based on user-supplied data. Moreover, the need for user input and transmission of vast amounts of data may undermine user experience quality and create latency for the remote enrollment management systems, as such systems incur substantial wait times associated with periods of receiving user-supplied data after user input of particular relevant input data. Thus, various existing remote enrollment management systems suffer from substantial security, reliability, user experience quality, and efficiency challenges that result from the need of such systems to receive vast amounts of user-supplied data during plan recommendation sessions.

To address the challenges associated with the security, reliability, user experience quality, and efficiency of various existing remote enrollment management systems, various embodiments of the present invention disclose techniques for performing enrollment recommendation based on preconfigured data stored locally on the remote enrollment management systems. Examples of the preconfigured data include demographic data associated with various member profiles, claim history data associated with various member profile, and/or the like. The disclosed embodiments utilize the preconfigured data to generate at least one of two sets of enrollment recommendations: enrollment recommendations based on comparing demographic features and transactional patterns across various members and enrollment recommendations based on comparing demographic features and transactional patterns on a per-member basis and vis-à-vis enrollment criteria for various health insurance plans.

By utilizing the above-noted techniques, various embodiments of the present invention enable reducing the need for real-time transmission of user-supplied input data prior to performing enrollment recommendation. In doing so, various embodiments of the present invention reduce the chance for exposure of sensitive member data to network security challenges by increasing use of locally-stored enrollment modeling data and plan definition data to generate enrollment recommendations. Moreover, increasing use of locally-stored enrollment modeling data and plan definition data to generate enrollment recommendations further eliminates delays associated with user input and transmission of data, thus increasing efficiency of enrollment management systems as well as enhancing user experience quality in such enrollment management systems. Thus, by disclosing techniques for increasing use of locally-stored enrollment modeling data and plan definition data to generate enrollment recommendations and thus reducing the need for real-time transmission of user-supplied input data prior to performing enrollment recommendation, various embodiments of the present invention make important technical contributions to security, reliability, user experience quality, and efficiency of the enroll management systems.

FIG. 4 is a data flow diagram of an example process 400 for remotely determining an enrollment recommendation 408 for a primary member profile from a pool of member profiles associated with the remote enrollment management system 101. Via the various steps/operations of process 400, the enrollment recommendation computing entity 106 can utilize preconfigured data (e.g., preconfigured enrollment modeling data stored in the enrollment modeling database 131 and preconfigured plan definition data stored in the plan definition database 132) to determine enrollment recommendations 408 for various member profiles by the remote enrollment management system 101 that communicates with client computing entities 102A-C of the various member profiles remotely and over the communication network 106. In doing so, the enrollment recommendation computing entity 106 can reduce the need for real-time transmission of enrollment input data by client computing entities 102A-C over the communication network 106, thus enhancing the data security of the architecture 100 utilized to perform remote determination of enrollment recommendations.

As depicted in FIG. 4, the cross-member enrollment recommendation unit 121 of the enrollment recommendation computing entity 106 is configured to retrieve cross-member enrollment modeling data 401 from the enrollment modeling database 131 and process the retrieved cross-member enrollment modeling data 401 to generate a cross-member enrollment recommendation 402 for the primary member profile. The cross-member enrollment modeling data 401 may include enrollment modeling data for the primary member profile as well as enrollment modeling data for each of one or more secondary member profiles (i.e., each member profile in the pool of member profiles associated with the remote enrollment management system 101 other than primary member profile). The cross-member enrollment recommendation 402 for the primary member profile may indicate one or more selected enrollment plans of a plurality of enrollment plans for the primary member profile, where the one or more selected enrollment plans for the primary member profile are selected based on the cross-member enrollment modeling data 401.

In some embodiments, to generate the cross-member enrollment recommendation 402 based on the cross-member enrollment modeling data 401, one or more of the following operations are performed by various components of the cross-member enrollment recommendation unit 121: (i) a member filtering subunit 411 of the cross-member enrollment recommendation unit 121 may determine one or more related member profiles 421 of the secondary member profiles, (ii) a training data generation subunit 412 of the cross-member enrollment recommendation unit 121 may generate training data 422 for each related member profile 421, (iii) a model generation subunit 413 of the cross-member enrollment recommendation unit 121 may generate a trained cross-member enrollment prediction model 423 based on the training data 422 for each related member profile 421, and (iv) a predictive inference subunit 414 of the cross-member enrollment recommendation unit 121 may generate the cross-member enrollment recommendation 402 based on the trained cross-member enrollment prediction model 423.

In some embodiments, to determine the related member profiles 421, the member filtering subunit 411 may compare at least a portion of the cross-member enrollment modeling data 401 for each secondary member profile with the cross-member enrollment modeling data 401 for the primary member profile in order to determine whether a measure of similarity between the cross-member enrollment modeling data 401 for each secondary member profile and the cross-member enrollment modeling data 401 for the primary member profile satisfies one or more related member identification criteria. For example, the member filtering subunit 411 may determine that a particular secondary member profile is a related member profile for the primary member profile when the member filtering subunit 411 determines that a threshold number (e.g., one, two, or all) of the following related member identification criteria are met with respect to the particular secondary member profile: (i) a transactional frequency category (e.g., a filed-claim count categorization) of the primary member profile and a transactional frequency category of the particular secondary member profile match, (ii) one or more dominant transactional patterns (e.g., one or more most-frequently-used service providers and/or one or more most-frequently-used prescription drugs) of the primary member profile and one or more dominant transactional patterns of the particular secondary member profile match, and (iii) one or more demographic features (e.g., age, gender, location, plan code, and/or the like) of the primary member profile and one or more demographic features of the particular secondary member profile match.

In some embodiments, to determine the related member profiles 421, the member filtering subunit 411 performs various steps/operations of the process depicted in FIG. 5. The process depicted in FIG. 5 begins at step/operation 501 when the member filtering subunit 411 retrieves the cross-member enrollment modeling data 401 for a particular secondary member profile. In some embodiments, the cross-member enrollment modeling data 401 for the particular secondary member profile include one or more transactional records (e.g., medical claims, health insurance claims, and/or the like) for the particular secondary member profile and one or more demographic information (e.g., health insurance profile information, gender information, age information, smoking habit information, and/or the like) for the particular secondary member profile. At step/operations 511-512, the member filtering subunit 411 determines one or more demographic features for the particular secondary member profile and determines whether the demographic features for the particular secondary member profile match corresponding demographic features for the primary member profile.

In some embodiments, when a particular demographic feature is a numerical feature, the member filtering subunit 411 determines that the particular demographic feature for the secondary member profile matches the particular demographic feature for the primary member profile if the member filtering subunit 411 determines that the particular demographic feature for the secondary member profile is within a predefined numerical range of the particular demographic feature for the primary member profile. In some embodiments, when a particular demographic feature is a categorical feature, the member filtering subunit 411 determines that the particular demographic feature for the secondary member profile matches the particular demographic feature for the primary member profile if the member filtering subunit 411 determines that the particular demographic feature for the secondary member profile is identical to the particular demographic feature for the primary member profile. In some embodiments, when a particular demographic feature is a categorical feature, the member filtering subunit 411 determines that the particular demographic feature for the secondary member profile matches the particular demographic feature for the primary member profile if the member filtering subunit 411 determines that a distance measure between that the particular demographic feature for the secondary member profile and the particular demographic feature for the primary member profile within a multi-dimensional feature embedding space is below a predefined distance threshold.

If the member filtering subunit 411 determines at step/operation 512 that the demographic features for the particular secondary member profile fail to match corresponding demographic features for the primary member profile, the member filtering subunit 411 concludes that the particular secondary member profile is not a related member profile for the primary member profile and loops back to step/operation 501 to retrieve cross-member enrollment modeling data 401 for a next secondary member profile. However, if the member filtering subunit 411 determines at step/operation 512 that the demographic features for the particular secondary member profile match corresponding demographic features for the primary member profile, the member filtering subunit 411 proceeds to steps/operations 521-522, in which the member filtering subunit 411 determines one or more dominant transactional patterns (e.g., one or more most frequently used medical providers, one or more most frequently used prescription drugs, one or more most frequently used pharmacies, one or more most frequently used medical operations, and/or the like) for the particular secondary member profile and determines whether the dominant transactional patterns for the particular secondary member profile match corresponding dominant transactional patterns for the primary member profile.

In some embodiments, to determine whether the dominant transactional patterns for the particular secondary member profile match corresponding dominant transactional patterns for the primary member profile, the member filtering subunit 411 identifies a list of dominant transactional patterns for the particular secondary member profile and a list of dominant transactional patterns for the primary member profile and proceeds to determine a similarity measure between the two lists. For example, the member filtering subunit 411 may determine the similarity measure between a list of dominant transactional patterns for the particular secondary member profile and a list of dominant transactional patterns for the primary member profile based on a count of shared transactional entities (e.g., medical providers, prescription drugs, and/or the like) associated with both of the two lists. As another example, the member filtering subunit 411 may determine the similarity measure between a list of dominant transactional patterns for the particular secondary member profile and a list of dominant transactional patterns for the primary member profile based on a weighed count of shared transactional entities associated with both of the two lists, where the weight of each shared transactional entity is determined based on a relative frequency of transactional records associated with the shared transactional entity among the transactional records of the primary member profile. As a further example, the member filtering subunit 411 may determine the similarity measure between a list of dominant transactional patterns for the particular secondary member profile and a list of dominant transactional patterns for the primary member profile based on a count of transactional entities (e.g., medical providers, prescription drugs, and/or the like) that appear on the a list of dominant transactional patterns for the primary member profile but fail to appear on the list of dominant transactional patterns for the particular secondary member profile.

If the member filtering subunit 411 determines at step/operation 522 that the dominant transactional patterns for the particular secondary member profile fail to match corresponding dominant transactional patterns for the primary member profile, the member filtering subunit 411 concludes that the particular secondary member profile is not a related member profile for the primary member profile and loops back to step/operation 501 to retrieve cross-member enrollment modeling data 401 for a next secondary member profile. However, if the member filtering subunit 411 determines at step/operation 522 that the dominant transactional patterns for the particular secondary member profile match corresponding dominant transactional patterns for the primary member profile, the member filtering subunit 411 proceeds to steps/operations 531-532, in which the member filtering subunit 411 determines a transactional frequency category for the particular secondary member profile and determines whether the transactional frequency category for the particular secondary member profile match the transactional frequency category for the primary member profile.

In some embodiments, the transactional frequency category for a member profile indicates a categorization of a count of transactional records (e.g., medical claims, health insurance claims, and/or the like) associated with the member profile, wherein the count of transactional records associated with the member profile is determined based on the cross-member enrollment modeling data 401 for the member profile. In some embodiments, the transactional frequency category for a member profile indicates a categorization of a weighed count of transactional records (e.g., medical claims, health insurance claims, and/or the like) associated with the member profile, wherein the weighed count of transactional records associated with the member profile is determined based on the cross-member enrollment modeling data 401 for the member profile, and wherein the weight for each transactional record used to determine the weighed count for the member profile may be determined based on how recent a timestamp associated with the transactional record is with respect to a current time.

In some embodiments, if the count and/or weighed count of transactional records associated with the member profile fails to exceed a lower threshold, the member filtering subunit 411 associates the member profile with a low transactional frequency category. In some embodiments, if the count and/or weighed count of transactional records associated with the member profile exceeds the lower threshold but fails to exceed a higher threshold, the member filtering subunit 411 associates the member profile with a medium transactional frequency category. In some embodiments, if the count and/or weighed count of transactional records associated with the member profile exceeds the higher threshold, the member filtering subunit 411 associates the member profile with a high transactional frequency category. In some embodiments, at least one of the lower threshold and the higher threshold are determined based on a distribution of transactional record counts across the pool of member profiles associated with the remote enrollment management system 101.

If the member filtering subunit 411 determines at step/operation 532 that the transactional frequency category for the particular secondary member profile fails to match the transactional frequency category for the primary member profile, the member filtering subunit 411 concludes that the particular secondary member profile is not a related member profile for the primary member profile and loops back to step/operation 501 to retrieve cross-member enrollment modeling data 401 for a next secondary member profile. However, if the member filtering subunit 411 determines at step/operation 532 that the transactional frequency category for the particular secondary member profile matches the transactional frequency category for the primary member profile, the member filtering subunit 411 proceeds to step/ operation 541, in which the member filtering subunit 411 determines that the particular secondary member profile is a related member profile for the primary member profile.

Returning to FIG. 4, the process 400 continues when the training data generation subunit 412 of the cross-member enrollment recommendation unit 121 generates training data 422 for each related member profile 421 determined by the member filtering subunit 411. In some embodiments, the training data 422 for a related member profile 421 include one or more training features for the related member profile 421 and a ground-truth enrollment recommendation for the related member profile. In some embodiments, the training features for the related member profile 421 are determined based on the cross-member enrollment modeling data 401 for the related member profile 421. In some embodiments, the ground-truth enrollment recommendation for the related member profile may be determined based on observations about real-world enrollment plan selection by the related member profile.

In some embodiments, to determine the training data 422 for a related member profile 421, the training data generation subunit 412 determines whether the cross-member enrollment modeling data 401 for the related member profile 421 (e.g., at least one of a transactional frequency category of the related member profile 421, one or more dominant transactional patterns of the related member profile 421, one or more demographic features of the related member profile 421, etc.) is compliant within an enrollment plan selected by the related member profile 421. If the training data generation subunit 412 determines that the cross-member enrollment modeling data 401 for the related member profile 421 is compliant within the enrollment plan selected by the related member profile 421, the training data generation subunit 412 generates training data 422 for the related member profile 421 using one or more of the feature extraction techniques described herein. However, if the training data generation subunit 412 determines that the cross-member enrollment modeling data 401 for the related member profile 421 is not compliant within the enrollment plan selected by the related member profile 421, the training data generation subunit 412 does not generate training data 422 for the related member profile 421, e.g., discards the cross-member enrollment modeling data 401 for the related member profile 421 as unreliable and/or "bad" training data.

In some embodiments, the training features for a related member profile 421 include at least one of the following: (i) one or more predictively critical transactional patterns for the particular related member profile 421 (e.g., whether the transactional records for the particular related member profile 421 indicate that the particular related member profile 421 has a history of critical surgeries) determined based on the one or more transactional patterns of the particular related member profile 421, (ii) one or more predictively frequent transactional frequency metrics for the particular related member profile (e.g., one or more of a count of health insurance claims by the particular related member profile 421 in which the particular related member profile 421 is the service recipient, a count of health insurance claims by the particular related member profile 421 in which a child dependent of the particular related member profile 421 is the service recipient, and a count of health insurance claims by the particular related member profile 421 in which a parent dependent of the particular related member profile 421 is the service recipient, and/or the like) determined based on the one or more transactional patterns of the particular related member profile 421, and (iii) one or more predictively critical demographic features (e.g., gender, location, plan code, and/or the like) for the particular related member profile 421 determined based at least in part on the one or more demographic features of the particular related member profile 421.

In some embodiments, to determine training features for a particular related member profile 421, the training data generation subunit 412 performs the steps/operations depicted in FIG. 6. The process depicted in FIG. 6 begins at step/operation 601 when the training data generation subunit 412 retrieves the cross-member enrollment modeling data 401 for the particular related member profile 421. In some embodiments, the cross-member enrollment modeling data 401 for a particular related member profile 421 include one or more transactional records (e.g., medical claims, health insurance claims, and/or the like) for the particular related member profile 421 and one or more demographic information (e.g., health insurance profile information, gender information, age information, smoking habit information, and/or the like) for the particular related member profile 421.

At step/operation 611, the training data generation subunit 412 determines one or more predictively critical transactional patterns for the particular related member profile 421 based on the cross-member enrollment modeling data 401 associated with the particular related member profile 421, e.g., based on transactional records associated with the associated with the particular related member profile 421. In some embodiments, the one or more predictively critical transactional patterns for the particular related member profile 421 include a first predictively critical transactional pattern indicating whether the particular related member profile 421 has a history of critical surgeries. In some embodiments, the one or more predictively critical transactional patterns for the particular related member profile 421 include a first predictively critical transactional pattern indicating whether the particular related member profile 421 has a history of procedures related to critical diseases.

At step/operation 621, the training data generation subunit 412 determines one or more predictively critical transactional frequency metrics for the particular related member profile 421 based on the cross-member enrollment modeling data 401 associated with the particular related member profile 421, e.g., based on transactional records associated with the particular related member profile 421. In some embodiments, the one or more predictively critical transactional frequency for the particular related member profile 421 indicate one or more of a count of health insurance claims by the particular related member profile 421 in which the particular related member profile 421 is the service recipient, a count of health insurance claims by the particular related member profile 421 in which a child dependent of the particular related member profile 421 is the service recipient, and a count of health insurance claims by the particular related member profile 421 in which a parent dependent of the particular related member profile 421 is the service recipient, and/or the like.

At step/operation 631, the training data generation subunit 412 determines one or more predictively critical demographic features for the particular related member profile 421 based on the cross-member enrollment modeling data 401 associated with the particular related member profile 421, e.g., based on demographic features associated with the associated with the particular related member profile 421. In some embodiments, the one or more predictively critical demographic features for the particular related member profile 421 indicate at least one of a gender for the particular related member profile 421, a location for the particular related member profile 421, a health insurance plan code for the particular related member profile 421, and/or the like.

Returning to FIG. 4, the model generation subunit 413 of the cross-member enrollment recommendation unit 121 generates a trained cross-member enrollment prediction model 423 based on the training data 422 for each related member profile 421. Moreover, the predictive inference subunit 414 of the cross-member enrollment recommendation unit 121 generates the cross-member enrollment recommendation 402 based on the trained cross-member enrollment prediction model 423 generated by the model generation subunit 413. The trained cross-member enrollment prediction model 423 may utilize one or more machine learning models, such as one or more regression machine learning models, neural network machine learning models, Bayesian network machine learning models, random forest machine learning models, support vector machine learning models, and/or the like. To generate the trained cross-member enrollment prediction model 423, the predictive inference subunit 414 may utilize one or more training algorithms, such as one or more optimization-based training algorithm (e.g., gradient descent, gradient descent with backpropagation, gradient descent with backpropagation through time, and/or the like).

In some embodiments, the trained cross-member enrollment prediction model 423 is configured to process one or more cross-member predictive features of the primary member profile in accordance with one or more model parameters and/or one or more model hyper-parameters for the trained cross-member enrollment prediction model 423 to generate the cross-member enrollment recommendation 402 for the primary member profile. In some embodiments, the one or more cross-member predictive features for the primary member profile are determined based on the cross-member enrollment modeling data 401 for the primary member profile. In some embodiments, the one or more cross-member predictive features for the primary member profile include one or more of the following: (i) one or more predictively critical transactional patterns for the primary member profile determined based on one or more transactional patterns of the primary member profile, (ii) one or more transactional frequency metrics for the primary member profile determined based on the or more transactional patterns of the primary member profile, and (iii) one or more predictively critical demographic features for the primary member profile determined based on one or more demographic features of the primary member profile.

An operational example of a trained cross-member enrollment prediction model 423 is presented in FIG. 7. The exemplary trained cross-member enrollment prediction model 423 depicted in FIG. 7 is a neural network model including an input layer 701, one or more fully-connected layers 702, and an output layer 704. Each layer 701-703 of the neural network model includes one or more neural network nodes. As depicted in FIG. 7, each neural network node 701A-C of the input layer 701 of the neural network model is configured to receive a corresponding cross-member predictive feature 711A-C for the primary member profile, process the corresponding cross-member predictive feature 711A-C for the primary member profile in accordance with one or more parameters to generate an activation value, and apply an activation function to the activation value to generate an output. Furthermore, each neural network node 702A-C, 703A-D in the fully-connected layers 702 is configured to receive outputs of nodes of a prior layer of the neural network model, process the received outputs in accordance with one or more parameters to generate an activation value, and apply an activation function to the activation value to generate an output. Moreover, the neural network node 704A in the output layer 704 of the neural network model is configured to receive outputs of the neural network nodes of the last fully-connected layer 702, process the received outputs in accordance with one or more parameters to generate an activation value, and apply an activation function to the activation value to generate the cross-member enrollment recommendation 402. In some embodiments, the cross-member enrollment recommendation 402 for the primary member profile is a selection of a predefined number (e.g., one) of a group of enrollment plans based on similarities among the pool of member profiles associated with the remote enrollment management system 101.

Returning to FIG. 4, the process 400 continues when the member-specific enrollment recommendation unit 122 of the enrollment recommendation computing entity 106 is configured to: (i) retrieve, from the enrollment modeling database 131, more recent enrollment modeling data 403 (e.g., enrollment modeling data for the past two years) for the primary member profile and less recent enrollment modeling data 404 (e.g., enrollment data for the past five years) for the primary member profile; (ii) retrieve, from the plan definition database 132, enrollment coverage criteria 407 for each enrollment plan of the plurality of enrollment plans; and (iii) process the more recent enrollment modeling data 403, the less recent enrollment modeling data 404, and the enrollment coverage criteria 407 to determine a member-specific enrollment recommendation 406 for the primary member profile. In some embodiments, the member-specific enrollment recommendation 406 for the primary member profile is a selection of a predefined number (e.g., one) of a group of enrollment plans based on transactional behaviors and/or demographic features of the primary member profile irrespective of the similarities among the pool of member profiles associated with the remote enrollment management system 101.

In some embodiments, to determine the member-specific enrollment recommendation 406 for the primary member profile, one or more of the following operations are performed by various components of the member-specific enrollment recommendation unit 122: (i) a dominant pattern detection subunit 431 of the member-specific enrollment recommendation unit 122 processes the more recent enrollment modeling data 403 to determine one or more dominant transactional patterns (e.g., one or more most frequently used medical providers, one or more most frequently used prescription drugs, one or more most frequently used pharmacies, one or more most frequently used medical operations, and/or the like) for the primary member profile; (ii) a frequency category detection subunit 431 processes the less recent enrollment modeling data 404 to determine a transactional frequency category for the primary member profile; and (iii) a plan compliance detection unit 433 processes the one or more dominant transactional patterns for the primary member profile, the transactional frequency category for the primary member profile, and the enrollment coverage criteria 407 to determine the member-specific enrollment recommendation 406 for the primary member profile.

In some embodiments, the dominant transactional patterns for the primary member profile and the transactional frequency category for the primary member profile define two aspects of coverage needs of the primary member profile. In particular, the dominant transactional patterns may identify the most significant medical providers, drugs, pharmacies, and/or the like likely to be needed by the primary member profile, while the transactional frequency category indicates an overall level of coverage need of the primary member profile. In some embodiments, the enrollment coverage criteria 407 for each enrollment plan indicate whether the enrollment plan covers the described aspects of the coverage needs of the primary member profile. For example, the enrollment coverage criteria 407 for a particular enrollment plan may indicate whether and under what terms the particular enrollment plan covers particular services, service providers, drugs, pharmacies, and/or the like. As another example, the enrollment coverage criteria 407 for a particular enrollment plan may indicate payment parameters of the enrollment plan such as the co-pay parameters of the particular enrollment plan, deductible parameters of the particular enrollment plan, and/or the like of the enrollment plan. In some embodiments, the payment parameters of a particular enrollment plan may affect the likely attractiveness of the particular enrollment plan for member profiles having diverse the transactional frequency categories. For example, a member profile with a high transactional frequency category may be interested in an enrollment plan with a lower co-pay.

In some embodiments, the plan compliance detection unit 433 detects one or more desirable enrollment plans whose coverage ratio for the one or more dominant transactional patterns determined by the dominant pattern detection subunit 431 exceeds a threshold value and/or whose corresponding transactional frequency category satisfies the transactional frequency category determined by the frequency category detection subunit 431. In some embodiments, if the plan compliance detection unit 433 detects a number of desirable enrollment plans whose count exceeds a predefined value (e.g., one) defining an allowed count of enrollment plans selected by the member-specific enrollment recommendation 406, the plan compliance detection unit 433 selects a subset of the desirable enrollment plans based on one or more of compliance measures, cost measures, and perceived utility measures of the desirable enrollment plans.

The process 400 ends when the recommendation generation unit 123 of the enrollment recommendation computing entity 106 determines the enrollment recommendation 408 based on the cross-member enrollment recommendation 402 and the member-specific enrollment recommendation 406. In some embodiments, the recommendation generation unit 123 presents both of the cross-member enrollment recommendation 402 and the member-specific enrollment recommendation 406 to the primary member profile using an enrollment recommendation user interface 800, such as the enrollment recommendation user interface 800 of FIG. 8. As depicted in FIG. 8, the exemplary enrollment recommendation user interface 800 depicts the cross-member enrollment recommendation 402 using the user interface element 801, the member-specific enrollment recommendation 406 using the user interface element 802, and coverage information for the member-specific enrollment recommendation 406 using the user interface element 803.

In some embodiments, the recommendation generation unit 123 displays information about the enrollment recommendation 408 using the recommended plan information user interface 900 of FIG. 9. As depicted in FIG. 9, the exemplary recommended plan information user interface 900 identifies distribution of transactional frequency categorizations for a recommended enrollment plan using the interface portion 901, a transactional frequency categorization for the recommended enrollment plan using column 902, a location association for the recommended enrollment plan using column 903, a plan identifier for the recommended enrollment plan using column 904, drug coverage information for the recommended enrollment plan using column 905, and provider coverage information for the recommended enrollment plan using column 906.

In some embodiments, at least some of the steps/operations of the process 400 may be performed as part of a remote enrollment recommendation session initiated by receiving an enrollment recommendation request for the enrollment recommendation 408. For example, all of the steps/operations 400, including steps/operations directed to generating a trained model, may be performed in real-time and as part of the remote enrollment recommendation session. In some embodiments, the enrollment recommendation computing entity 106 is configured to not receive any enrollment modeling data from a remote end-user during the remote enrollment recommendation session. In some embodiments, end-user interaction with the enrollment recommendation computing entity 106 during the remote enrollment recommendation session is limited to providing the enrollment recommendation request that initiates the remote enrollment recommendation session and receiving an indication of the enrollment recommendation 408 (e.g., an enrollment recommendation user interface). In some embodiments, display of an enrollment recommendation user interface terminates the remote enrollment recommendation session.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
accessing, by one or more processors, a cross-member enrollment prediction model from a cross-member enrollment recommendation unit, wherein the cross-member enrollment prediction model is generated based at least in part on a portion of second enrollment modeling data that comprises one or more transactional records or demographic information for one or more of a plurality of secondary member profiles that are related to a primary member profile based at least in part on first enrollment modeling data for the primary member profile and the second enrollment modeling data for the plurality of secondary member profiles with respect to (i) a transactional frequency category, (ii) one or more dominant transactional patterns, and (iii) one or more demographic features;
determining, by the one or more processors and via the cross-member enrollment recommendation unit, a cross-member enrollment recommendation with respect to the primary member profile based at least in part on the cross-member enrollment prediction model and one or more cross-member predictive features of the first enrollment modeling data;
determining, by the one or more processors and via a member-specific enrollment recommendation unit, a member-specific enrollment recommendation with respect to the primary member profile based at least in part on one or more member-specific features that are determined based at least in part on the first enrollment modeling data and one or more enrollment coverage criteria for a plurality of enrollment plans; and providing, by the one or more processors and via a recommendation generation unit to a remote client device, the cross-member enrollment recommendation and the member-specific enrollment recommendation to an enrollment recommendation user interface at the remote client device.

2. The computer-implemented method of claim 1, wherein the second enrollment modeling data comprises one or more transactional records for the plurality of secondary member profiles and the one or more demographic features.

3. The computer-implemented method of claim 1 further comprising:
 determining, for a secondary member profile of the plurality of secondary member profiles, a transactional frequency category based at least in part on one or more transactional records for the secondary member profile;
 determining, for the secondary member profile, one or more dominant transactional patterns based at least in part on the one or more transactional records for the secondary member profile; and
 determining whether the secondary member profile is related to the primary member profile based at least in part on: (i) whether one or more demographic features for the primary member profile match one or more demographic features for the secondary member profile, (ii) whether a transactional frequency category for the primary member profile matches a transactional frequency category for the secondary member profile, and (iii) whether one or more dominant transactional patterns for the primary member profile match one or more dominant transactional patterns for the secondary member profile.

4. The computer-implemented method of claim 1 further comprising determining one or more training features for a secondary member profile of the plurality of secondary member profiles by determining the one or more training features based at least in part on: (i) one or more predictively critical transactional patterns for the secondary member profile that are based at least in part on one or more transactional patterns of the secondary member profile, (ii) one or more predictively frequent transactional frequency metrics for the secondary member profile that are based at least in part on the one or more transactional patterns of the secondary member profile, and (iii) one or more predictively critical demographic features for the secondary member profile that are based at least in part on the one or more demographic features of the secondary member profile.

5. The computer-implemented method of claim 1 further comprising determining one or more cross-member features based at least in part on: (i) one or more predictively critical transactional patterns for the primary member profile that are based at least in part on one or more transactional patterns of the primary member profile, (ii) one or more transactional frequency metrics for the primary member profile that are based at least in part on the one or more transactional patterns of the primary member profile, and (iii) one or more predictively critical demographic features for the primary member profile that are based at least in part on the one or more demographic features of the primary member profile.

6. The computer-implemented method of claim 1 further comprising determining one or more member-specific features for the primary member profile by:
 determining one or more dominant transactional patterns for the primary member profile based at least in part on one or more transactional records for the primary member profile; and
 determining a transactional count frequency for the primary member profile based at least in part on the one or more transactional records.

7. The computer-implemented method of claim 6, wherein determining the one or more dominant transactional patterns for the primary member profile comprises:
 determining one or more dominant service providers associated with the primary member profile; and
 determining one or more dominant prescription drugs associated with the primary member profile.

8. The computer-implemented method of claim 6, wherein:
 determining the one or more dominant transactional patterns for the primary member profile comprises determining one or more transactional patterns based at least in part on a first temporal subset of the one or more transactional records for the primary member profile, and
 determining the transactional count frequency for the primary member profile comprises determining the transactional count frequency based at least in part on a second temporal subset of the one or more transactional records for the primary member profile, the first temporal subset is associated with a first temporal range, the second temporal subset is associated with a second temporal range, and the first temporal range is more recent than the second temporal range.

9. The computer-implemented method of claim 8, wherein the first temporal subset comprises a most recent two years.

10. The computer-implemented method of claim 8, wherein the first temporal subset comprises a most recent five years.

11. A system comprising one or more processors and at least one memory storing processor-executable instructions that, when executed by any of the one or more processors, causes the one or more processors to perform operations comprising:
 accessing a cross-member enrollment prediction model from a cross-member enrollment recommendation unit, wherein the cross-member enrollment prediction model is generated based at least in part on a portion of second enrollment modeling data that comprises one or more transactional records or demographic information for one or more of a plurality of secondary member profiles that are related to a primary member profile based at least in part on first enrollment modeling data for the primary member profile and the second enrollment modeling data for the plurality of secondary member profiles with respect to (i) a transactional frequency category, (ii) one or more dominant transactional patterns, and (iii) one or more demographic features;
 determining, via the cross-member enrollment recommendation unit, a cross-member enrollment recommendation with respect to the primary member profile based at least in part on the cross-member enrollment prediction model and one or more cross-member predictive features of the first enrollment modeling data;
 determining, via a member-specific enrollment recommendation unit, a member-specific enrollment recommendation with respect to the primary member profile based at least in part on one or more member-specific features that are determined based at least in part on the first enrollment modeling data and one or more enrollment coverage criteria for a plurality of enrollment plans;
and
providing, via a recommendation generation unit to a remote client device, the cross-member enrollment recommendation and the member-specific enrollment recommendation to an enrollment recommendation user interface at the remote client device.

12. The system of claim 11, wherein the second enrollment modeling data comprises one or more transactional records for the plurality of secondary member profiles and the one or more demographic features.

13. The system of claim 11, wherein the operations further comprise:
determining, for a secondary member profile of the plurality of secondary member profiles, a transactional frequency category based at least in part on one or more transactional records for the secondary member profile;
determining, for the secondary member profile, one or more dominant transactional patterns based at least in part on the one or more transactional records for the secondary member profile; and
determining whether the secondary member profile is related to the primary member profile based at least in part on: (i) whether one or more demographic features for the primary member profile match one or more demographic features for the secondary member profile, (ii) whether a transactional frequency category for the primary member profile matches a transactional frequency category for the secondary member profile, and (iii) whether one or more dominant transactional patterns for the primary member profile match one or more dominant transactional patterns for the secondary member profile.

14. The system of claim 11, wherein the operations further comprise determining one or more training features based at least in part on: (i) one or more predictively critical transactional patterns for a secondary member profile that are based at least in part on one or more transactional patterns of the secondary member profile, (ii) one or more predictively frequent transactional frequency metrics for the secondary member profile that are based at least in part on the one or more transactional patterns of the secondary member profile, and (iii) one or more predictively critical demographic features for the secondary member profile that are based at least in part on the one or more demographic features of the secondary member profile.

15. The system of claim 11, wherein the operations further comprise determining one or more cross-member features based at least in part on: (i) one or more predictively critical transactional patterns for the primary member profile that are based at least in part on one or more transactional patterns of the primary member profile, (ii) one or more transactional frequency metrics for the primary member profile that are based at least in part on the one or more transactional patterns of the primary member profile, and (iii) one or more predictively critical demographic features for the primary member profile that are based at least in part on the one or more demographic features of the primary member profile.

16. The system of claim 11, wherein the operations further comprise:
determining one or more dominant transactional patterns for the primary member profile based at least in part on one or more transactional records for the primary member profile; and
determining a transactional count frequency for the primary member profile based at least in part on the one or more transactional records.

17. The system of claim 16, wherein the operations further comprise:
determining one or more dominant service providers associated with the primary member profile; and
determining one or more dominant prescription drugs associated with the primary member profile.

18. One or more non-transitory computer-readable storage media including instructions that, when executed by one or more processors, cause the one or more processors to perform operations comprising:
accessing a cross-member enrollment prediction model from a cross-member enrollment recommendation unit, wherein the cross-member enrollment prediction model is generated based at least in part on a portion of second enrollment modeling data that comprises one or more transactional records or demographic information for one or more of a plurality of secondary member profiles that are related to a primary member profile based at least in part on first enrollment modeling data for the primary member profile and the second enrollment modeling data for the plurality of secondary member profiles with respect to (i) a transactional frequency category, (ii) one or more dominant transactional patterns, and (iii) one or more demographic features;
determining, via the cross-member enrollment recommendation unit, a cross-member enrollment recommendation with respect to the primary member profile based at least in part on the cross-member enrollment prediction model and one or more cross-member predictive features of the first enrollment modeling data;
determining, via a member-specific enrollment recommendation unit, a member-specific enrollment recommendation with respect to the primary member profile based at least in part on one or more member-specific features that are determined based at least in part on the first enrollment modeling data and one or more enrollment coverage criteria for a plurality of enrollment plans;
and
providing, via a recommendation generation unit to a remote client device, the cross-member enrollment recommendation and the member-specific enrollment recommendation to an enrollment recommendation user interface at the remote client device.

19. The one or more non-transitory computer-readable storage media of claim 18, wherein the second enrollment modeling data comprises one or more transactional records for the plurality of secondary member profiles and the one or more demographic features.

20. The one or more non-transitory computer-readable storage media of claim 18, wherein the operations further comprise:
determining, for a secondary member profile of the plurality of secondary member profiles, a transactional frequency category based at least in part on one or more transactional records for the secondary member profile;
determining, for the secondary member profile, one or more dominant transactional patterns based at least in part on the one or more transactional records for the secondary member profile; and determining whether the secondary member profile is related to the primary member profile based at least in part on: (i) whether one or more demographic features for the primary member profile match one or more demographic features for the secondary member profile, (ii) whether a transactional frequency category for the primary member profile matches a transactional frequency category for the secondary member profile, and (iii) whether one or more dominant transactional patterns for the primary member profile match one or more dominant transactional patterns for the secondary member profile.

\* \* \* \* \*